United States Patent [19]

Gundlach et al.

[11] Patent Number: 5,380,356

[45] Date of Patent: Jan. 10, 1995

[54] QUARTZ-FREE POWDERED MAGMATIC NEPHELINE ROCK MATERIAL FOR THE SURFACE TREATMENT OF DENTAL PARTS, ESPECIALLY GRINDING, POLISHING AND/OR BLASTING MATERIAL

[75] Inventors: Hans-Werner Gundlach, Bremen; Peter Stroncik, Osterholz-Scharmbeck, both of Germany

[73] Assignee: BEGO Bremer Goldschlägerei Wilh. Herbst GmbH & Co., Bremen, Germany

[21] Appl. No.: 940,211

[22] Filed: Sep. 8, 1992

[30] Foreign Application Priority Data

Sep. 7, 1991 [DE] Germany ............... 4129870
Nov. 7, 1991 [DE] Germany ............... 4136592

[51] Int. Cl.⁶ ................. A61K 6/00; A61K 7/30
[52] U.S. Cl. ...................... 106/3; 106/35; 424/52
[58] Field of Search .............. 106/3, 35; 424/52

[56] References Cited

U.S. PATENT DOCUMENTS

| | | | |
|---|---|---|---|
| 2,489,848 | 11/1949 | Bacon et al. | 252/138 |
| 2,559,122 | 7/1951 | Hessel et al. | 51/298 |
| 3,690,366 | 9/1972 | Schwartz | 164/25 |
| 3,892,843 | 7/1975 | Muhler et al. | 424/52 |
| 4,044,507 | 8/1977 | Cox et al. | 51/424 |
| 4,658,826 | 4/1987 | Weaver | 128/640 |
| 5,037,453 | 8/1991 | Narayanan et al. | 51/307 |

FOREIGN PATENT DOCUMENTS

| | | |
|---|---|---|
| 954849 | 11/1956 | Germany . |
| 931908 | 7/1975 | Germany . |
| 2747852 | 5/1979 | Germany . |
| 2814806 | 7/1979 | Germany . |
| 3144298 | 5/1983 | Germany . |
| 8523483338 | 2/1985 | Japan . |
| WO8102670 | 10/1981 | WIPO . |

OTHER PUBLICATIONS

Derwent Publications Ltd., London, GB; AN 85-180799 & JP-A-60 108 500 (Lion Corp.) Jun. 13, 1985.

Derwent Publications Ltd., London, GB AN 91-196387 & JP-A-3 120 204 (Mizusawa Chemical) May 22, 1991.

Berry and Mason, *Mineralogy Concepts Descriptions Determinations* (pp. 218-223, 363, 492) no month available 1959.

Primary Examiner—Paul Lieberman
Assistant Examiner—Margaret Einsmann
Attorney, Agent, or Firm—Sughrue, Mion, Zinn, Macpeak & Seas

[57] ABSTRACT

The invention is directed to the creation of a material which does not have the hazardous properties of prior art materials containing quartz. In the material according to the invention, quartz is replaced with a quartz-free magmatic rock, especially nepheline syenite. Surprisingly, the magmatic rock in powdered form attains nearly the same treatment results as conventional materials which contain quartz. The material according to the invention is particularly suitable for polishing and blasting dental parts, especially those parts which are made of plastic material.

8 Claims, No Drawings

QUARTZ-FREE POWDERED MAGMATIC NEPHELINE ROCK MATERIAL FOR THE SURFACE TREATMENT OF DENTAL PARTS, ESPECIALLY GRINDING, POLISHING AND/OR BLASTING MATERIAL

BACKGROUND OF THE INVENTION

The invention relates to a material for the surface treatment of dental parts, especially to a grinding and-/or polishing material with solid substances which are included in a preferably liquid or paste-like mass, to a blasting material composed of preferably granular or powdered solid substances, and to the special usage of the material.

These type of materials serve for finishing the surface of dental parts such as dental prostheses, crowns, dental bridges, model castings and/or facing ceramics. Such materials, especially grinding, polishing and/or blasting materials, usually contain solid or filler substances composed of quartz. Quartz is a crystalline silicon dioxide. It has been revealed that people who often work with quartz contract a typical disease, the so-called silicosis. Accordingly, quartz constitutes a health hazard.

SUMMARY OF THE INVENTION

The invention is therefore based on the object to create a material for the surface treatment of dental parts, especially grinding, polishing and/or blasting material. which is not a health hazard but still has the same properties as the known materials of this type.

A material for the surface treatment of dental parts which attains this object is characterized in that the solid substances are formed from a powder of quartz-free magmatic rock. The resulting material does not comprise crystalline silica and, surprisingly, has essentially the same effects which are attained with grinding, polishing or blasting materials which comprise solid or filler substances composed of quartz. These materials, namely grinding, polishing and/or blasting materials, are particularly suitable for the surface treatment in the art of dental technology, especially for grinding, polishing and/or blasting dental parts.

Suitable quartz-free magmatic rocks are foyaites, phonolites, nepheline basaltes and in particular nepheline syenites. Especially nepheline syenites exhibit nearly the same grinding, polishing and blasting properties as the materials of this type which comprise quartz.

The use of nepheline syenites with a particle size of 2 to 300 $\mu$m, especially 60 to 150 $\mu$m has turned out to be of particular advantage. Especially for grinding, polishing and blasting purposes, nepheline syenites with such a particle size exhibit a very good efficiency and durability, almost equal to pure crystalline silica, i.e. quartz.

DESCRIPTION OF PREFERRED EMBODIMENTS

According to a preferred development of the invention, especially the grinding and/or polishing materials in which the nepheline syenites are included in a liquid or pastelike mass, contain an additional bactericide. Expediently, this bactericide is mixed into the liquid or paste-like mass. As a result, the material has desinfectant properties which are of particular advantage when the material is used in the art of dental technology.

The invention will be described below with reference to preferred examples:

A grinding or polishing material which is most suitably used in dental laboratories, and especially for polishing plastic parts of the dental area, such as dental prostheses, crowns, bridges or the like, is composed of:
100 l water
100 kg glycerine
2 l defoaming agent (for example silicone oil)
1000 kg nepheline syenite
0.3 to 2.5 kg bactericide additives.

Suitable bactericide additives are quaternary amines, phenol derivatives and/or parabens. Materials which do not need to have a bactericidal effect do not have to be provided with bactericide additives.

Nepheline syenite in granular or powdered form with a particle size of between 2 and 300 $\mu$m is used as a blasting material. The particle size or particle size subrange which is to be selected from the foregoing particle size range depends on the material which is to be treated or the desired surface quality. It would also be possible to use a mixture of nepheline syenite of different particle sizes or particle size groups as a blasting material.

In this respect, a suitable nepheline syenite would be $NaAlSiO_4$, $KAlSi_3O_8$ or
$NaAlSiO_4$, $(Na,Ca) AlSi_3O_8$ In the above examples, the nepheline syenite is present in powdered form with a particle size of 2 to 300 $\mu$m, especially 60 to 150 $\mu$m. Its colour corresponds to the natural colour. It would also be possible to prepare materials according to the above examples in which nepheline syenite is replaced by foyaites, phonolites or nepheline basaltes of the same quantity and in the same particle size range.

We claim:

1. A polishing material for the surface treatment of dental parts, and consisting primarily of solid substances in a liquid or paste-like mass, wherein the solid substances are made of quartz-free magmatic nepheline syenite rock, wherein the quartz-free magmatic nepheline syenite rock is in fine-granular or powdered form and has a particle size of 2 to 300 $\mu$m, and wherein said material is further composed of:
   water;
   glycerine;
   a defoaming agent; and
   bactericide additives.

2. A process for performing a surface treatment of dental parts by using the material as claimed in claim 1 for polishing dental parts selected from a group consisting of dental prostheses, crowns, bridges, model castings and facing ceramics.

3. The polishing material as claimed in claim 1, wherein the quartz-free nepheline syenite rock has a particle size of 60 $\mu$m to 150 $\mu$m.

4. The material as claimed in claim 1, wherein said material is composed of
   100 l water;
   100 kg glycerine;
   2 l defoaming agent;
   1000 kg nepheline syenite; and
   0.3 to 2.5 kg bactericide additives.

5. A process for polishing a surface of dental parts selected from a group consisting of dental prostheses, crowns, bridges, model castings and facing ceramics, said process comprising using a material composed of quartz-free magmatic nepheline syenite rock, in a liquid or paste-like mass, to polish the surface, said material being further composed of water, glycerine, a defoaming agent and bactericide additives.

6. The process as claimed in claim 5, wherein the dental parts are plastic.

7. The process as claimed in claim 5, wherein said material is composed of:
100 l water;
100 kg glycerine;
2 l defoaming agent;
1000 kg nepheline syenite; and
0.3 to 2.5 kg bactericide additives.

8. The process as claimed in claim 5, wherein the nepheline syenite is selected from the group consisting of $NaAlSiO_4$, $KAlSi_3O_8$, and $NaAlSiO_4$, $(Na,Ca)AlSi_3O_8$.

* * * * *